United States Patent

(12) United States Patent
Orlandi

(10) Patent No.: US 6,713,491 B2
(45) Date of Patent: Mar. 30, 2004

(54) HETEROCYCLIC DERIVATIVES

(75) Inventor: Alessandra Orlandi, Lainate (IT)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/148,434

(22) PCT Filed: Jul. 12, 2000

(86) PCT No.: PCT/EP00/12335

§ 371 (c)(1),
(2), (4) Date: Aug. 12, 1999

(87) PCT Pub. No.: WO01/42238

PCT Pub. Date: Jun. 14, 2001

(65) Prior Publication Data

US 2003/0008899 A1 Jan. 9, 2003

(30) Foreign Application Priority Data

Dec. 8, 1999 (GB) ............................................. 9929037

(51) Int. Cl.⁷ ...................... A61K 31/47; C07D 215/02
(52) U.S. Cl. .................... 514/314; 546/167; 514/314
(58) Field of Search ................... 546/165, 167; 514/314

(56) References Cited

U.S. PATENT DOCUMENTS

| 5,231,102 A | 7/1993 | Baker et al. |
| 5,977,136 A | 11/1999 | Di Fabio et al. |
| 6,362,199 B1 * | 3/2002 | Di Fabio ................ 514/314 |
| 6,413,985 B1 * | 7/2002 | Di Fabio ................ 514/314 |

FOREIGN PATENT DOCUMENTS

| EP | 0 672 662 | | 9/1995 | |
| WO | WO 97/12870Q | | 4/1997 | |
| WO | WO 98/07704 A | | 2/1999 | |
| WO | WO 99/64411 | * | 8/1999 | ............... 514/314 |
| WO | WO 99/64411 | | 12/1999 | |

OTHER PUBLICATIONS

Powder Coating, The Complete Finisher's Hardbook, Ed by N.P. Liberto pp. 108–110, 1994.*

Solomans, Graham and Fryhle, Craig. "Organic Chemistry: seventh edition." Chapter 5:Stereochemsitry:Chiral Molecules. pp. 184–198.

* cited by examiner

Primary Examiner—Alan L. Rotman
Assistant Examiner—Janet L Coppins
(74) Attorney, Agent, or Firm—Lorie Ann Morgan

(57) ABSTRACT

The present invention relates to a novel salt of enantiomer A of 7-chloro-4-(2-oxo-1-phenyl-3-pyrrolidinylidene)-1,2,3,4-tetrahydro-2-quinoline carboxylic acid or a solvate thereof, to processes for its preparation, to pharmaceutical compositions containing it and to its use in therapy and in particularly its use as medicine for antagonising the effects of excitatory amino acids upon the NMDA receptor complex.

22 Claims, No Drawings

HETEROCYCLIC DERIVATIVES

CROSS REFERENCE TO RELATED APPLICATIONS

This application was filed pursuant to 35 U.S.C. §371 as a U.S. National Phase Application of International Application No. PCT/EP00/12335, filed Dec. 7, 2000, which claims priority to Great Britain Priority Patent Application Serial No. 9929037.1, filed Dec. 8, 1999.

The present invention relates to a novel salt of enantiomer A of 7-chloro-4-(2-oxo-1-phenyl-3-pyrrolidinylidene)-1,2,3,4-tetrahydro-2-quinoline carboxylic acid or a solvate thereof, to processes for its preparation, to pharmaceutical compositions containing it and to its use in therapy and in particularly its use as medicine for antagonising the effects of excitatory amino acids upon the NMDA receptor complex.

The compound 7-chloro-4-(2-oxo-1-phenyl-3-pyrrolidinylidene)-1,2,3,4-tetrahydro-2-quinolinecarboxylic acid of formula (I) is inter alia described in WO 99/64411 which also refers to physiologically acceptable salts thereof and more particularly it describes an enantiomer of the compound of formula (I), which is referred to therein as enantiomer A and a sodium salt thereof.

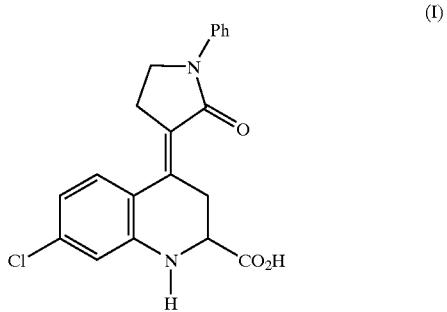

(I)

The enantiomer A of 7-chloro-4-(2-oxo-1-phenyl-3-pyrrolidinylidene)-1,2,3,4-tetrahydro-2-quinolinecarboxylic acid is a particularly potent antagonist of the NMDA receptor complex, and for its use in medicine there exists a need for the compound to be prepared in a form suitable for ease of isolation in a large scale manufacture and for ease of formulating into an acceptable product for administration to patients. These requirements are not conveniently met by either enantiomer A or sodium salt thereof.

DETAILED DESCRIPTION OF THE INVENTION

It has been found that the meglumine salt of enantiomer A can readily be prepared and isolated suitable in a pure form by a process that is suitable for use on a large scale, and the said salt can be conveniently obtained with the required high degree of purity and good stability and thus fulfils the exacting criteria required in the preparation of pharmaceutical compositions for administration to patients.

The present invention thus provides the meglumine salt of enantiomer A of 7-chloro-4-(2-oxo-1-phenyl-3-pyrrolidinylidene)-1,2,3,4-tetrahydro-2-quinolinecarboxylic acid of formula (I) or a solvate (e.g. hydrate) thereof (hereinafter referred to as the compound of the invention).

Particularly the invention provides the meglumine salt of enantiomer A of 7-chloro-4-(2-oxo-1-phenyl-3-pyrrolidinylidene)-1,2,3,4-tetrahydro-2-quinolinecarboxylic acid in a crystalline form.

More particularly, according to one embodiment, the invention provides for a hydrate crystalline form of the the meglumine salt of enantiomer A of 7-chloro-4-(2-oxo-1-phenyl-3-pyrrolidinylidene)-1,2,3,4-tetrahydro-2-quinolinecarboxylic acid (hereinafter referred to as form 1), characterised by the following X-ray powder diffraction pattern expressed as 2 Theta ($\theta$) value

| Angle 2 $\theta$ | | |
|---|---|---|
| 4.356 | 18.641 | 22.993 |
| 11.263 | 18.725 | 23.681 |
| 11.659 | 20.546 | 25.043 |
| 12.757 | 21.362 | 25.598 |
| 12.877 | 22.234 | 26.823 |
| 13.962 | 22.379 | 28.753 |
| 15.482 | 22.801 | |
| 17.242 | 22.921 | |

According to a further embodiment of the invention there is provided for another crystalline form of the meglumine salt of enantiomer A of 7-chloro-4-(2-oxo-1-phenyl-3-pyrrolidinylidene)-1,2,3,4-tetrahydro-2-quinolinecarboxylic acid (hereinafter referred to as form 2) characterised by the following X-ray powder diffraction pattern expressed as 2 Theta ($\theta$) value

| Angle 2 $\theta$ | | |
|---|---|---|
| 5.480 | 19.553 | 25.225 |
| 8.233 | 20.505 | 25.802 |
| 10.942 | 21.939 | 26.484 |
| 15.299 | 22.787 | 27.524 |
| 16.424 | 23.154 | 27.865 |
| 16.658 | 23.381 | 28.547 |
| 19.116 | 24.194 | 38.345 |

The compound of the invention can be obtained in more than one crystalline form. It is to be understood that the invention includes all such forms or mixture thereof. The compound of the invention is an excitatory amino acid antagonist. More particularly it is a potent antagonist at the strychnine insensitive glycine binding site associated with the NMDA receptor complex. As such it is a potent antagonist of the NMDA receptor complex. This compound is therefore useful in the treatment or prevention of neurotoxic damage or neurodegenerative diseases. Thus the compound is useful for the treatment of neurotoxic injury which follows cerebral stroke, thromboembolic stroke, hemorrhagic stroke, cerebral ischemia, cerebral vasospam, hypoglycemia, amnesia, hypoxia, anoxia, perinatal asphyxia cardiac arrest. The compound of the invention is useful in the treatment of chronic neurodegenerative diseases such as: Huntingdon's disease, Alzheimer's senile dementia, amyotrophic lateral sclerosis, Glutaric Acidaemia type, multiinfarct dementia, status epilecticus, contusive injuries (e.g. spinal cord injury and head injury), viral infection induced neurodegeration (e.g. AIDS, encephalopaties), Down syndrome, ocular neurodegeneration (e.g glaucoma), epilepsy, schizophrenia, depression, migraine, headaches including cluster headaches and or tension headaches, anxiety, pain (e.g inflammatory pain and neuropathic pain), neurogenic bladder, irritable bowel syndrome and or visceral hyperalgesia, emesis, irritative bladder disturbances, drug dependency, including withdrawal symptoms from alcohol, cocaine, opiates, nicotine (e.g. smoking cessation) benzodiazepines and inhibition of tolerance induced by opioids (i.e. morphine).

The potent and selective action of the compound of the invention at the strychnine-insensitive glycine binding site present on the NMDA receptor complex may be readily determined using conventional test procedures. Thus the ability to bind at the strychnine insensitive glycine binding site was determined using the procedure of Kishimoto H et al., J Neurochem 1981, 37, 1015–1024. The selectivity of the action of compounds of the invention for the strychnine insensitive glycine site was confirmed in studies at other ionotropic known excitatory amino acid receptors. Thus the compound of the invention was found to show little or no affinity for the kainic acid (kainate) receptor, a-amino-3-hydroxy-5-methyl-4-isoxazole-proprionic acid (AMPA) receptor or at the NMDA binding site.

The compound of the invention may be found to inhibit NMDA induced convulsions in mice using the procedure Chiamulera C et al., Psychopharmacology (1990), 102, 551–552.

The neuroprotective activity of the compound of the invention may be demonstrated in the middle cerebral artery occlusion preparation in mice, using the procedure described by Chiamulera C. et al., European Journal of Pharmacology, 216 (1992) pp. 335–336.

The ability of compound of the invention to alleviate withdrawal symptoms from nicotine following smoking cessation may be demonstrated in conventional tests of nicotine induced relapse using the procedure described in C. Chiamulera et al., Arch. Pharmacol., 358, 1998.

The ability of the compound of the invention to inhibit pain may be demonstrated in conventional analgesic screen such as those described by Dubuisson and Dennis, *Pain*, 1977, 4:161–174; J. J. Bennett and J. K Xue, *Pain*, 1988, 41, 87–107.

The invention also provides for the use of the compound of the invention for use in therapy and in particular use as medicine for antagonising the effects of excitatory amino acids upon the NMDA receptor complex.

The invention also provides for the use of the compound of the invention for the manufacture of a medicament for antagonising the effects of excitatory amino acids upon the NMDA receptor complex.

According to a further aspect, the invention also provides for a method for antagonising the effects of excitatory amino acids upon the NMDA receptor complex, comprising administering to a patient in need thereof an antagonistic amount of the compound of the invention.

It will be appreciated by those skilled in the art that reference herein to treatment extends to prophylactics as well as the treatment of established diseases or symptoms.

It will further be appreciated that the amount of the compound of the invention required for use in treatment will vary with the nature of the condition being treated, the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 20–100 mg, preferably 60–80 mg per day. For oral administration a daily dose will typically be within the range 200–800 mg, e.g. 400–600 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising the compound of the invention together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant or rectal administration.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable propellants, such as dichlorodifluoromethane, trichlorofluoromethane, dichloro-tetrafluoroethane, carbon dioxide or other suitable gases, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in, for example, capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

A further aspect of the invention provides a process for the preparation of the compound of the invention.

Thus in one embodiment compound of the invention may be prepared by treating a solution of the enantiomer A (I) with meglumine in a suitable solvent such as aprotic solvent (i.e. actetone, tetrahydrofuran) or alkanol such as ethanol.

The invention further provides a method for producing the compound of the invention in a crystalline form.

Thus the compound of the invention in hydrate crystalline form (form 1) may be prepared by treating a solution of enantiomer A of 7-chloro-4-(2-oxo-1-phenyl-3-pyrrolidinylidene)-1,2,3,4-tetrahydro-2-quinolinecarboxylic acid in ethanol with meglumine dissolved in water. The reaction is carried out at room temperature and in an environment free of the compound of the invention in crystalline form 2.

The crystalline form 2 may obtained by crystallisation of the compound of the invention from a mixture of water and a water miscible organic antisolvent. Suitable water miscible organic antisolvents for use in the crystallisation include alkanol (e.g. ethanol, IMS (ethanol/methanol 95/5) or isopropanol), acetone or acetonitrile. A particularly convenient water miscible organic antisolvent is ethanol or acetone.

Conveniently the crystallisation process is carried out by adding the antisolvent to a solution of the compound of the invention dissolved in water.

In a further embodiment of the process, the crystalline form 2 may be obtained by crystallisation of the compound of the invention from a mixture of suitable organic solvents. Thus, form 2 may be obtained by dissolution of the compound of the invention in a suitable organic solvent (i.e. N,N-dimethylformamide or 1-methyl-2-pyrrolidone) followed by treatment with a suitable organic antisolvent such as alkanol (e.g. ethanol, IMS (ethanol/methanol 95/5) or isopropanol) or an aprotic solvent (e.g. acetone, tetrahydrofuran dichloromethane, ethylacetate, toluene, or acetonitrile). The process is preferably carried out at a temperature ranging between 20–45° C.

The enantiomer A of the compound of formula (I) may be prepared according to the processes described in WO 99/64411 which is incorporated by reference. In a preferred embodiment, the enantiomer A of the compound of formula (I) may be prepared by stereoselective enzymatic hydrolysis of compounds of formula (II) with ferulic acid esterase in a pure form.

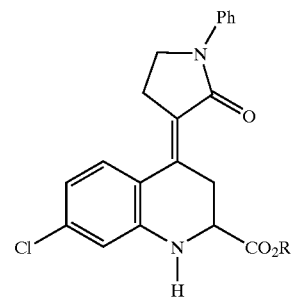

(II)

wherein R is a carboxyl protecting group.

Suitable carboxyl protecting group R for use in this reaction includes $C_{1-4}$ alkyl such as methyl, ethyl, propyl, butyl or arylmethyl groups such as benzyl, nitrobenzyl or trityl.

The reaction is conveniently carried out in an aprotic solvent such as DMSO, tetrahydrofuran in the presence of a suitable aqueous buffer (i.e. citrate, phosphate buffer or $CaCl2$). If required, a solubilising agent such as Tween-80 may be added to the reaction mixture.

In a further process the enzyme may be immobilized and the reaction is carried out in essentially "neat" water-saturated organic solvents such as methyl tert-butyl ether or tert-amyl alcohol.

The stereoselective enzymatic hydrolysis of compounds of formula (II) with ferulic acid esterase in a pure form is novel and represents a further aspect of the invention.

The invention also extends to the meglumine salt of enantiomer A of 7-chloro-4-(2-oxo-1-phenyl-3-pyrrolidinylidene)-1,2,3,4-tetrahydro-2-quinolinecarboxylic acid of formula (I) or a solvate thereof when prepared from the enantiomer A of formula (I) which has been obtained by stereoselective enzymatic hydrolysis of compounds of formula (II) with ferulic acid esterase in a pure form.

Meglumine is commercially available (Aldrich).

In the Intermediates and Example unless otherwise stated: Melting points (m.p.) were determined on a Gallenkamp m.p. apparatus and are uncorrected. All temperatures refer to ° C. Proton Magnetic Resonance ($^1$H-NMR) spectra were recorded at 500 MHz, chemical shifts are reported in ppm downfield (d) from $Me_4Si$, used as internal standard, and are assigned as singlets (s), doublets (d), doublets of doublets (dd), triplets (t), quartets (q) or multiplets (m). Column chromathography was carried out over silica gel (Merck AG Darmstaadt, Germany). DBU=1,8-diazobicyclo [5,4,0] undec-7-ene.

The X-ray powder diffraction pattern of a crystalline form of the compound of the invention was obtained by loading the sample into the diffractometer (Siemens D5005 X-ray diffractometer equipped with θ/θ goniometer, scintillation counter and graphite monochromator. The diffractometer was set up with the instrumental parameters given below:

Instrumental Parameters
MONOCHROMATIC RADIATION: Cu-1.54056/1.54439
2θ RANGE: 20–40° 2θ
GENERATOR VOLTAGE/CURRENT: 40 kV/50 mA
STEP SIZE: 0.02° 2θ
TIME PER STEP: 2 $sec^{-1}$ ROTATION: on
DIVERGENCE/ANTISCATTERING SLIT: variable
SAMPLE HOLDER: round cavity on low-background plate.

The spectrum obtained was analysed using the data evaluation software EVA3.0.

Enantiomer A refers to a single enantiomer whose absolute stereo chemistry was not determined

INTERMEDIATE 1

(±)-Ethyl 2-(5-chloro-2-iodoanilino)-4-pentenoate

To a solution of 2-iodo 4 chloro aniline (9.1 g) in dry toluene (150 ml) ethyl glyoxylate (50% solution in toluene, 14.6 ml) and $MgSO_4$ (2 g) were added and the resulting suspension was refluxed overnight. It was then filtered and concentrated to dryness under high vacuum at 50° C. for 1.5 h. The resulting brown oil was dissolved in dichloromethane (150 ml) cooled to −78° C. and $TiCl_4$ (99.995% purity, 4 ml) was added via syringe. The suspension was stirred 15 min at −78° C., then allowed to warm to rt over 15 min before being cooled again to −78° C. Allyltributyltin (17 ml) was then added and the reaction allowed to proceed for 1 h. The black solution was poured into 200 ml of ethyl acetate and washed first with a saturated solution of $NH_4Cl$ (2×150 ml), then with water and brine. The organic phase was dried and concentrated to give the crude product, which was purified by column chromatography (cyclohexane, then cyclohexane/ethyl acetate 98/2) to give the title compound (10.4 g) as a colourless oil.

NMR ($CDCl_3$) δ (ppm) 7.57 (d, 1H), 6.49 (dd, 1H), 6.45 (dd, 1H), 5.79 (m, 1H), 5.25 (dd, 1H) 5.24 (dd, 1H), 4.83 (d, 1H), 4.25 (q,2H), 4.13 (m, 1H), 2.66 (m, 2H), 1.30 (t, 3H)

INTERMEDIATE 2

(±)-Ethyl 2-(5-chloro-2-iodoanilino)-4-oxobutanoate

A solution of intermediate 1 (5.2 g) in dichloromethane (150 ml) was cooled to −78° C. and ozone was bubbled through it until the clear solution became brick-red. At this point the flux of ozone was interrupted and the solution was purged with nitrogen for a few minutes. Triphenyl phosphine (7.1 g) was added and stirring continued for 1.5 h, without control of the temperature. The resulting solution was poured into 200 ml of ethyl acetate and washed first with a saturated solution of $NH_4Cl$ (2×150 ml), then with water and brine. The organic phase was dried and concentrated to give the crude product, which was purified by column chromatography (cyclohexane/ethyl acetate 80/20) to give the title compound (2.4 g) as a colourless oil. $^1$NMR (DMSO) δ (ppm) 9.80 (t, 1H), 7.57 (d, 1H), 6.55 (d, 1H), 6.51 (dd, 1H), 4.99 (d, 1H), 4.46 (m, 1H), 4.24 (q, 2H), 3.08 (m, 2H), 1.28 (t, 3H)

INTERMEDIATE 3

(±) E-Ethyl 2-(5-chloro-2-iodoanilino-4-(2-oxo-1-phenyl-3-pyrrolidinylidene) butanoate (3a);(±)-Z-Ethyl 2-(5-chloro-2-iodoanilino)-4-(2-oxo-1-phenyl-3-pyrrolidinylidene) butanoate(3b)

To a solution of intermediate 2 (2.4 g) in acetonitrile (100 ml) at r.t. Tributyl (2-oxo-1-phenylpyrrolidin-1-yl) phosphonium bromide (3.7 g) and DBU (13 ml) were added and stirring was continued overnight at −20° C. The crude solution was poured into 200 ml of ethyl acetate and washed with a saturated solution of $NH_4Cl$ (2×150 ml), then with water and brine. The organic phase was dried and concentrated to give the crude product as a 4/1 mixture of 3a/3b compounds. Purification by column chromatography (cyclohexane/ethyl acetate 80/20) gave the title 3a (2.16 g) and the 3b (0.5 g) compounds as colourless oils.

INTERMEDIATE 3a $^1$NMR ($CDCl_3$) δ (ppm) 7.72 (d, 2H), 7.56 (d, 1H), 7.38 (t, 2H), 7.16 (t, 1H), 6.6 (m, 1H), 6.50 (dd, 1H), 6.49 (d, 1H), 4.88 (d, 1H), 4.26 (m, 3H), 3.87 (t, 2H), 2.79 (m, 4H), 1.30 (t, 3H)

INTERMEDIATE 3b $^1$NMR ($CDCl_3$) δ (ppm) 7.69 (d, 2H), 7.52 (d, 1H), 7.38 (t, 2H), 7.17 (t, 1H), 6.47 (d, 1H), 6.44 (dd, 1H), 5.98 (m, 1H), 5.00 (d, 1H), 4.22 (m, 2H), 4.13 (m, 1H), 3.84 (t, 2H), 3.2–3.6 (m, 2H), 2.85 (m, 2H), 1.26 (t, 3H)

INTERMEDIATE 4

(±)-Ethyl 7-chloro-4-(2-oxo-1-phenyl-3-pyrrolidinylidene)-1,2,3,4-tetrahydro-2-quinolinecarboxylate To a solution of intermediate 3b (370 g) in toluene (5.2 lit), Triethylamine (248 ml), Triphenylphosphine (7.4 g) and $PdCl_2$ (2.52 g) were added. The resulting solution was warmed to 100° C. and stirred for 2 h. The suspension was chilled to 20–25° C. and toluene (2.6 ml) was added.

The reaction mixture was washed with $NH_4Cl$ 8% (3×5.2 lit) and water (5.2 lit). The organic layer was filtered over a celite pad and it was washed with toluene (1 lit); then it was distilled under vacuum (T=50° C.; P=60 mbar) to reach 6.3 lit. After cooling to T=20–25° C., isooctane (5.2 lit) was dropped over 30 min. The precipitate was stirred for 2 h 30 min then it was filtered and washed with a mixture toluene/isooctane 1/1 (1.85 lit). The yellow solid was dried in vacuum at T=40° C. for 18 h to obtain the title compound as a yellow solid (210 g).

m.p. 160–162° C.

$^1$NMR (DMSO): 7.72 (m, 2H); 7.39 (m, 2H); 7.20 (d, 2H); 7.15 (m, 2H); 6.96 (dd, 1H); 6.74 (d, 1H); 6.57 (dd, 1H); 4.29 (dd, 1H); 4.21 (m, 1H); 4.02 (m, 1H); 3.93 (m, 1H); 3.82 (m, 1H); 3.69 (m, 1H); 3.20 (m, 1H). 2.92 (m, 2H); 2.92 (m, 2H); 0.93 (t, 3H).

EXAMPLE 1

(−)Meglumine salt of enantiomer A of 7-chloro-4-(2-oxo-1-phenyl-3-pyrrolidinylidene)-1,2,3,4-tetrahydro-2-quinolinecarboxylic Acid (Form 2)

Method A 16.5 g of Lipase Amano AP12 (*Aspergillus niger* lipase) were suspended in 360 ml of 0.1M citrate buffer (pH=3) in a stirred vessel at 15° C. 27.5 g of intermediate 4 were dissolved in 190 ml of dimethyl sulphoxide at 20° C. and this solution added into the vessel under vigorous stirring. The mixture was stirred at 37° C. for 24 hrs and 27.5 g of filter aid (Dicalite) were added to the reaction mixture which was then cooled to 20° C. After addition of 275 ml of aq. 0.2M hydrochloric acid the mixture was cooled to +6° C. and then filtered. The filter cake was washed with 140 ml of aq. 0.2M hydrochloric acid and 140 ml of water before being dried. The so obtained dried filter cake (55 g) was extracted at 20° C. with 660 ml of acetone, then filtered off washing with 220 ml of acetone. To the filtrate, 33 ml of an aqueous solution of meglumine (0.2 g/ml) were added. The so obtained suspension was digested and the solid filtered and washed with 275 ml of acetone. After drying the crude title compound was obtained as a yellow solid (16.2 g). 4 g of this crude compound were then dissolved in 10 ml of water by heating at 50° C., then 110 ml of EtOH were added. After digestion at 20° C. the solid was filtered and dried to obtain the purified title compound as a yellow solid (3.75 g), m.p. 186° C.

The title compound (5 mg) was dissolved in 1 ml of a mixture D$_2$O/DMSO 95/5.

$^1$H-NMR (D$_2$O/DMSO 95/5) δ (ppm) 7.44 (2H, d), 7.37 (2H, t), 7.19 (1H, t), 7.16 (1H, d), 6.66 (1H, d), 6.58 (1H, dd), 3.96 (1H, m), 3.78–3.50 (8H, m), 3.46 (1H, dd), 3.99 (1H, dd), 3.10 (1H, dd), 3.05 (1H, d), 3.02 (2H, m), 2.64 (3H, s).

[α]$_D$=−321.7; λ=598 nm; 20° C. conc mg/ml 0.12% solvent=methanol.

Method B

To a warmed at 35° C. 0.1M Sodium citrate buffer obtained by mixing a 0.1M aqueous solution (412 ml) of citric acid and a 0.1M aqueous solution (196 ml) of trisodic citrate dihydrate into a jacketed reactor, an aqueous solution (Conc=40 mg/ml) of the enzyme ferulic acid esterase (19.6 ml) and dimethyl sulfoxide (98 ml) were added. To the resulting solution, a solution of Intermediate 4 (49 g) in dimethyl sulfoxide (270 ml) was added. Then the mixture was stirred at 37–38° C. for 24 hrs.

After cooling at 20° C. the reaction mixture was extracted twice with 2-butanone (1470 mL) and the organic layer was washed with a 6% sodium chloride aqueous solution (2×980 ml) and a 25% sodium chloride aqueous solution (392 ml) then, after addition of further 2-butanone (490 ml) the solvent was distilled off at atmospheric pressure to a residual 200 ml volume. Then acetone (1323 ml) was added to the mixture and a 20% aqueous meglumine solution (60 ml) was dropped into the mixture. The resulting suspension was stirred for 1 h, then filtered, washed with acetone (490 ml) and dried at 40° C. under vacuum for ca 16 hrs to obtain the crude title compound as a yellow solid (26.9 g).

26.8 g of the crude title compound was dissolved with water (107, 2 ml) at 55° C. and after filtration cooled at 45° C. Then acetone (268 ml) was dropped under stirring and the mixture seeded with the title compound. Acetone (402 ml) was then further added and the resulting slurry was stirred at 20° C. for 1 hr and at 2° C. for 2 hrs and then solid was filtered washed with acetone (134 ml) and dried under vacuum at 40° C. for ca 16 hrs to obtain the title compound (23 g), m.p. 185–187° C.

TABLE 1

The X-ray powder diffraction pattern of the product of Example 1 in terms of 'd' spacings is as follows

| Angle (°2θ) | d value (A) |
| --- | --- |
| 5.480 | 16.114 |
| 8.233 | 10.731 |
| 10.942 | 8.079 |
| 15.299 | 5.787 |
| 16.424 | 5.393 |
| 16.658 | 5.317 |
| 19.116 | 4.639 |
| 19.553 | 4.536 |
| 20.505 | 4.328 |
| 21.939 | 4.048 |
| 22.787 | 3.899 |
| 23.154 | 3.838 |
| 23.381 | 3.801 |
| 24.194 | 3.676 |
| 25.225 | 3.528 |

TABLE 1-continued

The X-ray powder diffraction pattern of the product of Example 1 in terms of 'd' spacings is as follows

| Angle (°2θ) | d value (A) |
| --- | --- |
| 25.802 | 3.450 |
| 26.484 | 3.363 |
| 27.524 | 3.238 |
| 27.865 | 3.199 |
| 28.547 | 3.124 |
| 38.345 | 2.346 |

EXAMPLE 2

(−)Meglumine salt of enantiomer A of 7-chloro-4-(2-oxo-1-phenyl-3-pyrrolidinylidene)-1,2,3,4-tetrahydro-2-quinolinecarboxylic Acid (Form 1)

(−)-Sodium 7-chloro4-(2-oxo-1-phenyl-3-pyrrolidinylidene)-1,2,3,4-tetrahydro-2-quinoline-carboxylate(2.5 g) was suspended in ethyl acetate (75 ml) and extracted with aqueous HCl 1.5N (25 ml). The organic layer was evaporated to dryness to obtain 7-chloro-4-(2-oxo-1-phenyl-3-pyrrolidinylidene)-1,2,3,4-tetrahydro-2-quinoline-2-carboxylic acid_as a white foam (2.3 g) which was dissolved in ethanol (69 ml) at 23° C. under nitrogen and then a solution of meglumine (1.25 g) in water (5.3) was added in 20 minutes. The suspension was stirred at 23° C. under nitrogen for 24 hours. The solid was filtered and dried at 40° C. for 20 hours (3.0 g), m.p. 112° C.

$^1$H-NMR (D$_2$O/DMSO 95/5) δ (ppm) 7.73 (2H, d), 7.38 (2H, t), 7.15 (1H, d), 7.13 (1H, t), 6.77 (1H, d), 6.45 (1H, dd), 6.40 (1H, bs), 4.10 (1H, bm), 3.79 (3H, m), 3.64 (1H, dd), 3.60 (1H, bm), 3.55 (1H, dd), 3.47 (1H, m), 3.40 (1H, d). 3.38 (1H, t), 3.16 (1H, m), 2.98 (1H, m), 2.85 (1H, m), 2.78 (1H, m), 2.70 (1H, bm), 2.42 (3H, s).

X ray powder diffraction data are reported in Table 2.

TABLE 2

The X-ray powder diffraction pattern of the product of Example 2 in terms of 'd' spacings is as follows

| Angle (°2θ) | d value (A) |
| --- | --- |
| 4.356 | 20.270 |
| 11.263 | 7.849 |
| 11.659 | 7.584 |
| 12.757 | 6.934 |
| 12.877 | 6.869 |
| 13.962 | 6.337 |
| 15.482 | 5.719 |
| 17.242 | 5.139 |
| 18.641 | 4.756 |
| 18.725 | 4.735 |
| 20.546 | 4.319 |
| 21.362 | 4.156 |
| 22.234 | 3.995 |
| 22.379 | 3.969 |
| 22.801 | 3.897 |
| 22.921 | 3.877 |
| 22.993 | 3.865 |
| 23.681 | 3.754 |
| 25.043 | 3.553 |
| 25.598 | 3.477 |
| 26.823 | 3.321 |
| 28.753 | 3.102 |

PHARMACY EXAMPLES

| A. Capsules/Tablets | |
| --- | --- |
| Active ingredient | 20.0 mg |
| Starch 1500 | 32.5 mg |
| Microcrystalline Cellulose | 200.0 mg |
| Croscarmellose Sodium | 6.0 mg |
| Magnesium Stearate | 1.5 mg |

The active ingredient is blended with the other excipients. The blend can be used to fill gelatin capsules or compressed to form tablets using appropriate punches. The tablets can be coated using conventional techniques and coatings.

| B. Tablets | |
| --- | --- |
| Active ingredient | 20.0 mg |
| Sorbitol | 200.0 mg |
| Microcrystalline Cellulose | 70.0 mg |
| Povidone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.

| C. Bolus | |
| --- | --- |
| Active ingredient | 0.1–32 mg/ml |
| Trometamol | 1.0–5.0 mg/ml |
| water for injection qs to | 1 ml |

The formulation may be packed in glass ampoules or vials and syringes with a rubber stopper and a plastic/metal overseal (vials only).

| D. Infusion | |
| --- | --- |
| Active ingredient | 0.01–3.2 mg/ml |
| Trometamol | 0.2–1.0 mg/ml |
| 5% dextrose injection qs to | 100 ml |

The formulation may be packed in glass vials or plastic bags.

No untoward effects have been observed when compound of the invention has been administred to mice at the pharmacological active doses.

What is claimed is:

1. (−) Meglumine salt of 7-chloro-4-(2-oxo-1-phenyl-3-pyrrolidinylidene)-1,2,3,4-tetrahydro-2-quinolinecarboxylic acid.

2. A crystalline form of the compound as claimed in claim 1.

3. A process for the preparation of a crystalline form as claimed in claim 2 which comprises crystallising the meglumine salt from a mixture of water and a water miscible organic solvent or from a mixture of suitable organic solvents.

4. A pharmaceutical composition comprising a compound as claimed in claim 1 in admixture with one or more physiologically acceptable carriers or excipients.

5. A method of treatment of a mammal for conditions where antagonising the effects of excitatory amino acids on the NMDA receptor complex is of therapeutic benefit, comprising administration of an effective amount of a compound as claimed in claim 1.

6. The method according to claim 5, wherein said mammal is man.

7. A method for selectively antagonising the strychnine insensitive glycine binding site associated with the NMDA receptor complex, said method comprising administration of a compound according to claim 1.

8. A method for the treatment or prophylaxis of neurotoxic damage or neurodegenerative diseases where antagonising the NMDA receptor complex is of therapeutic benefit, in a mammal, said method comprising administrator of an effective amount of a compound according to claim 1.

9. The method according to claim 8, wherein said mammal is man.

10. A method for the treatment or prophylaxis of migraine in a mammal, said method comprising administration of an effective amount of a compound according to claim 1.

11. The method according to claim 10, wherein said mammal is man.

12. A method for the treatment or prophylaxis of withdrawal symptoms from nicotine in a mammal, said method comprising administration of an effective amount of a compound according to claim 1.

13. The method according to claim 12, wherein said mammal is man.

14. A method for the treatment or phophylaxis of withdrawal symptoms from alcohol in a mammal, said method comprising administration of an effective amount of a compound according to claim 1.

15. The method according to claim 14, wherein said mammal is man.

16. A method for the treatment or prophylaxis of pain in a mammal, said method comprising administration of an effective amount of a compound according to claim 1.

17. The method according to claim 16, wherein said mammal is man.

18. A method for the treatment or prophylaxis of inflammatory pain in a mammal, said method comprising administration of an effective amount of a compound according to claim 1.

19. The method according to claim 18, wherein said mammal is man.

20. A method for the treatment or prophylaxis of neuropathic pain in a mammal, said method comprising administration of an effective amount of a compound according to claim 1.

21. The method according to claim 20, wherein said mammal is man.

22. A crystalline form of a compound according to claim 1 having the X-ray powder diffraction pattern expressed in terms of angles 2θ and d spacings as follows:

| Angle (°2θ) | d value (Å) |
| --- | --- |
| 5.480 | 16.114 |
| 8.233 | 10.731 |
| 10.942 | 8.079 |
| 15.299 | 5.787 |
| 16.424 | 5.393 |
| 16.658 | 5.317 |
| 19.116 | 4.639 |
| 19.553 | 4.536 |
| 20.505 | 4.328 |
| 21.939 | 4.048 |
| 22.787 | 3.899 |
| 23.154 | 3.838 |
| 23.381 | 3.801 |

-continued

| Angle (°2θ) | d value (Å) |
| --- | --- |
| 24.194 | 3.676 |
| 25.225 | 3.528 |
| 25.802 | 3.450 |
| 26.484 | 3.363 |
| 27.524 | 3.238 |
| 27.865 | 3.199 |
| 28.547 | 3.124 |
| 38.345 | 2.346 |

* * * * *